US010969358B2

(12) United States Patent
Hansen et al.

(10) Patent No.: US 10,969,358 B2
(45) Date of Patent: Apr. 6, 2021

(54) METHOD FOR CORRECTING CREA SENSOR FOR CALCIUM INHIBITION

(71) Applicant: Radiometer Medical ApS, Brønshøj (DK)

(72) Inventors: Thomas Steen Hansen, Herlev (DK); Thomas Pedersen Nygaard, Herlev (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 0 days.

(21) Appl. No.: 15/742,121

(22) PCT Filed: Jun. 20, 2016

(86) PCT No.: PCT/EP2016/064182
§ 371 (c)(1),
(2) Date: Jan. 5, 2018

(87) PCT Pub. No.: WO2017/005479
PCT Pub. Date: Jan. 12, 2017

(65) Prior Publication Data
US 2018/0202963 A1 Jul. 19, 2018

(30) Foreign Application Priority Data
Jul. 6, 2015 (DK) .......................... PA 2015 00384

(51) Int. Cl.
G01N 27/327 (2006.01)
G01N 33/70 (2006.01)
C12Q 1/00 (2006.01)

(52) U.S. Cl.
CPC ......... G01N 27/3274 (2013.01); C12Q 1/001 (2013.01); C12Q 1/005 (2013.01);
(Continued)

(58) Field of Classification Search
CPC .......................... G01N 27/3274; G01N 33/70
See application file for complete search history.

(56) References Cited

U.S. PATENT DOCUMENTS 7,888,061 B2* 2/2011 Kjaer ................. C12Q 1/34
435/25
2006/0275859 A1* 12/2006 Kjaer ................. C12Q 1/002
435/25

(Continued)

FOREIGN PATENT DOCUMENTS

CN 1219676 A 6/1999
CN 101175999 A 5/2008

(Continued)

OTHER PUBLICATIONS

International Search Report for International Application No. PCT/EP2016/064182, dated Sep. 30, 2016.

(Continued)

Primary Examiner — Luan V Van
Assistant Examiner — Caitlyn Mingyun Sun
(74) Attorney, Agent, or Firm — Finnegan, Henderson, Farabow, Garrett & Dunner

(57) ABSTRACT

A method of calibrating a device for measuring the concentration of creatinine in a sample including one or more enzyme modulators, the device comprising an enzyme layer, the method comprising: determining sensitivities of the device for each of one or more calibration solutions; determining a degree of modulation for the sample to be measured, determining a degree of modulation for each calibration solution; wherein said determining of each of the degrees of modulation comprises estimating the concentration of an enzyme modulator in the enzyme layer of the device; and calculating the sensitivity of the device for the sample, wherein the said calculating comprises adjusting the sensitivity of the device for each calibration solution by a (Continued)

factor comprising the determined degrees of modulation of the sample and the calibration solution.

13 Claims, 4 Drawing Sheets

(52) U.S. Cl.
CPC . *C12Y 105/03001* (2013.01); *C12Y 305/0201* (2013.01); *C12Y 305/03003* (2013.01); *G01N 33/70* (2013.01); *G01N 2333/90683* (2013.01); *G01N 2333/978* (2013.01); *G01N 2333/986* (2013.01); *G01N 2496/00* (2013.01)

(56) References Cited

U.S. PATENT DOCUMENTS

| | | |
|---|---|---|
| 2008/0039702 A1 | 2/2008 | Hayter et al. |
| 2008/0173064 A1 | 7/2008 | Schaffar et al. |
| 2011/0060300 A1* | 3/2011 | Weig ................ A61F 5/451 604/319 |
| 2012/0181189 A1 | 7/2012 | Merchant |

FOREIGN PATENT DOCUMENTS

| | | |
|---|---|---|
| CN | 107110813 A | 8/2017 |
| JP | 2000-507457 A | 6/2000 |
| JP | 2004-506224 A | 2/2004 |
| JP | 2008-541104 A | 11/2008 |
| JP | 2009-271075 A | 11/2009 |
| JP | 2017-533012 A | 11/2017 |
| WO | WO 02/097415 A2 | 12/2002 |
| WO | WO 2016/096683 A1 | 6/2016 |

OTHER PUBLICATIONS

Written Opinion of the International Searching Authority for International Application No. PCT/EP2016/064182.

* cited by examiner

METHOD FOR CORRECTING CREA SENSOR FOR CALCIUM INHIBITION

This application is a national stage filing under 35 U.S.C. § 371 of International Application No. PCT/EP2016/064182, filed on Jun. 20, 2016, which claims priority of Danish Patent Application No. PA 2015 00384, filed Jul. 6, 2015. The contents of these applications are each incorporated herein by reference.

FIELD OF THE INVENTION

The invention relates to methods for calibrating creatine and creatinine measuring devices, particularly in the presence of enzyme modulators.

BACKGROUND

Techniques for measuring the concentration of creatinine (Crn) and creatine (Cr) have uses in medicine, for example in monitoring renal disease and in monitoring performance athletes. The concentration of Cr (cCr) and the concentration of Crn (cCrn) in an aqueous solution can be determined by amperometric measurement. Two sensors can be used in the measurement of cCrn: the Crea A sensor, which detects Cr; and the Crea B sensor, which detects both Cr and Crn. The cCrn is based on the difference between the Crea A and Crea B sensor measurements.

Sensors typically use enzymes to convert Crn and Cr into measurable products, such as hydrogen peroxide which can be detected in an amperometric system. In order to determine cCrn and cCr in unknown samples with sufficient accuracy, the Crea A and Crea B sensors must be calibrated in order to determine their actual sensitivities.

However, the presence of enzyme modulators in a sample can modulate (i.e. increase or decrease) the activity of the enzymes in the sensor and thereby its sensitivity. Therefore, a sensor calibrated with a calibration solution that has a different amount or type of enzyme modulator than the sample being measured may yield inaccurate results.

Enzyme modulators can occur naturally in samples being measured, and may occur in unpredictable amounts. For example, calcium ($Ca^{2+}$) and bicarbonate ($HCO_3^-$) are enzyme inhibitors and are endogenous to blood, and different people will have different concentrations of these modulators in their blood. Therefore, the presence of these modulators may affect the measurements made.

Furthermore, some modulators such as $Ca^{2+}$ diffuse very slowly into the sensor. As such, when performing a measurement on a new sample, the effects of the residual $Ca^{2+}$ from an earlier sample may also affect the results. Given the slow rate of diffusion, a long rinse would be required to remove any residual modulator from a previous sample, which would increase the cycle time between samples.

There is, therefore, an unmet need for an efficient method of calibrating Cr and/or Crn sensors to take into account different levels of enzyme modulation in the sensors, while keeping the cycle times as short as possible.

SUMMARY OF THE INVENTION

In a first aspect of the present invention, the applicant makes available a method of calibrating a device for measuring the concentration of Cr and/or Crn in a sample including one or more enzyme modulators, the device comprising an enzyme layer, the method comprising: determining sensitivities of the device for each of one or more calibration solutions; determining a degree of modulation for the sample to be measured, determining a degree of modulation for each calibration solution; wherein said determining of each of the degrees of modulation comprises estimating the concentration of an enzyme modulator in the enzyme layer of the device; and calculating the sensitivity of the device for the sample, wherein the said calculating comprises adjusting the sensitivity of the device for each calibration solution by a factor comprising the determined degrees of modulation of the sample and the calibration solution.

By determining degrees of modulation in samples and calibration solutions, it is possible to calibrate the measurements to correct any effect the modulators may have on the readings, thereby resulting in more accurate results. Certain modulators may remain in the enzyme layer of the calibrating device and may therefore affect the results, therefore said degrees of modulation may take into account the concentrations or amounts of modulator that are estimated to be in the enzyme layer.

In some example embodiments prior to the determining a degree of modulation for the sample, the method further comprising: aspirating an earlier sample in the device or, in another embodiment, the method is performed on a sample previously aspirated in the device. The proposed solution is particularly beneficial where earlier samples have been aspirated, as the aspiration of these samples may result in increased levels of enzyme modulator remaining in the enzyme layer between measurements. As the proposed solution takes the amount of enzyme modulator in the enzyme layer into account, the proposed solution is particularly well equipped for making measurements after an earlier sample has been measured.

In some example embodiments, the period of time from aspirating the earlier sample to measuring the concentration of Crn in the sample is less than two minutes, and preferably 1 minute. It may be advantageous to keep the time between two samples short (such as below 2 or 1 minute) as this would increase the number of samples that can be measured in a given time. However, when rinses are short (e.g. less than 2 minutes) there may be enough enzyme modulator remaining to affect the accuracy of the result. The proposed solution takes into account the amount of enzyme modulator remaining in the enzyme layer after a short rinse. The proposed solution makes it possible to make accurate measurements despite enzyme modulator remaining in the enzyme layer.

In some example embodiments, said estimating the concentration of an enzyme modulator comprises determining a period of time elapsed since aspirating the earlier sample. As measurements are not necessarily performed during steady state, the amount of enzyme modulator may be time dependent. Therefore, by measuring the time elapsed since a previous measurement of a sample (and therefore a previous measurement of enzyme modulator), it is possible to estimate the amount of enzyme modulator remaining after the given time period.

In some example embodiments, estimating the concentration of an enzyme modulator further comprises estimating a change in concentration of an enzyme modulator in the enzyme layer of the device during the determined period of time.

In some example embodiments, said estimating a change in concentration comprises evaluating an exponential decay term, wherein the time constant of the exponential decay term is related to the rate of transfer of enzyme modulator into or out of the enzyme layer.

In some example embodiments, prior to the determining the degree of modulation for the sample, the method further comprising: estimating an earlier concentration of enzyme modulator in the enzyme layer after aspirating the earlier sample, wherein the determination of the degrees of modulation utilises the earlier concentration.

In some example embodiments, the method further comprising measuring a concentration of enzyme modulator in the sample, wherein the determination of the degree of modulation for the sample utilises the concentration of enzyme modulator of the sample.

In some example embodiments, the method further comprising receiving a concentration of enzyme modulator in each calibration solution, wherein the determination of the degrees of modulation for the calibration solutions utilises one or more of the concentrations of enzyme modulator of each calibration solution.

In some example embodiments, prior to the determining a degree of modulation for the sample, the method further comprises performing a rinse in the device.

In some example embodiments, the method further comprising receiving a concentration of enzyme modulator of the rinse solution used in the rinse, wherein the determination of the degrees of modulation utilises the concentration of enzyme modulator of a rinse solution.

In some example embodiments, the one or more enzyme modulators include $Ca^{2+}$, $Mg^{2+}$, and salts thereof.

In some example embodiments, the one or more enzyme modulators inhibit enzyme activity.

In some example embodiments, said determining the sensitivities of the device for each calibration solutions comprises calculating a ratio between an output of the device in the calibration solution and a concentration of Cr and/or Crn in the calibration solution.

In some example embodiments, said factor further comprises a ratio between two of said determined sensitivities of calibration solutions, wherein each calibration solution has a different amount of enzyme modulator In some example embodiments, the device is a Cr and/or Crn sensor.

According to another aspect of the present invention, a computer readable medium is provided comprising instructions which when executed by one or more processors of an electronic device, cause the electronic device to operate in accordance with any of the aforementioned methods.

According to another aspect of the present invention, an electronic device is provided comprising: one or more processors; and memory comprising instructions which when executed by one or more of the processors cause the electronic device to operate in accordance with any of the aforementioned methods.

BRIEF DESCRIPTIONS OF DRAWINGS

Examples of the present proposed apparatus will now be described in detail with reference to the accompanying drawings, in which.

DETAILED DISCLOSURE

Figure 1:
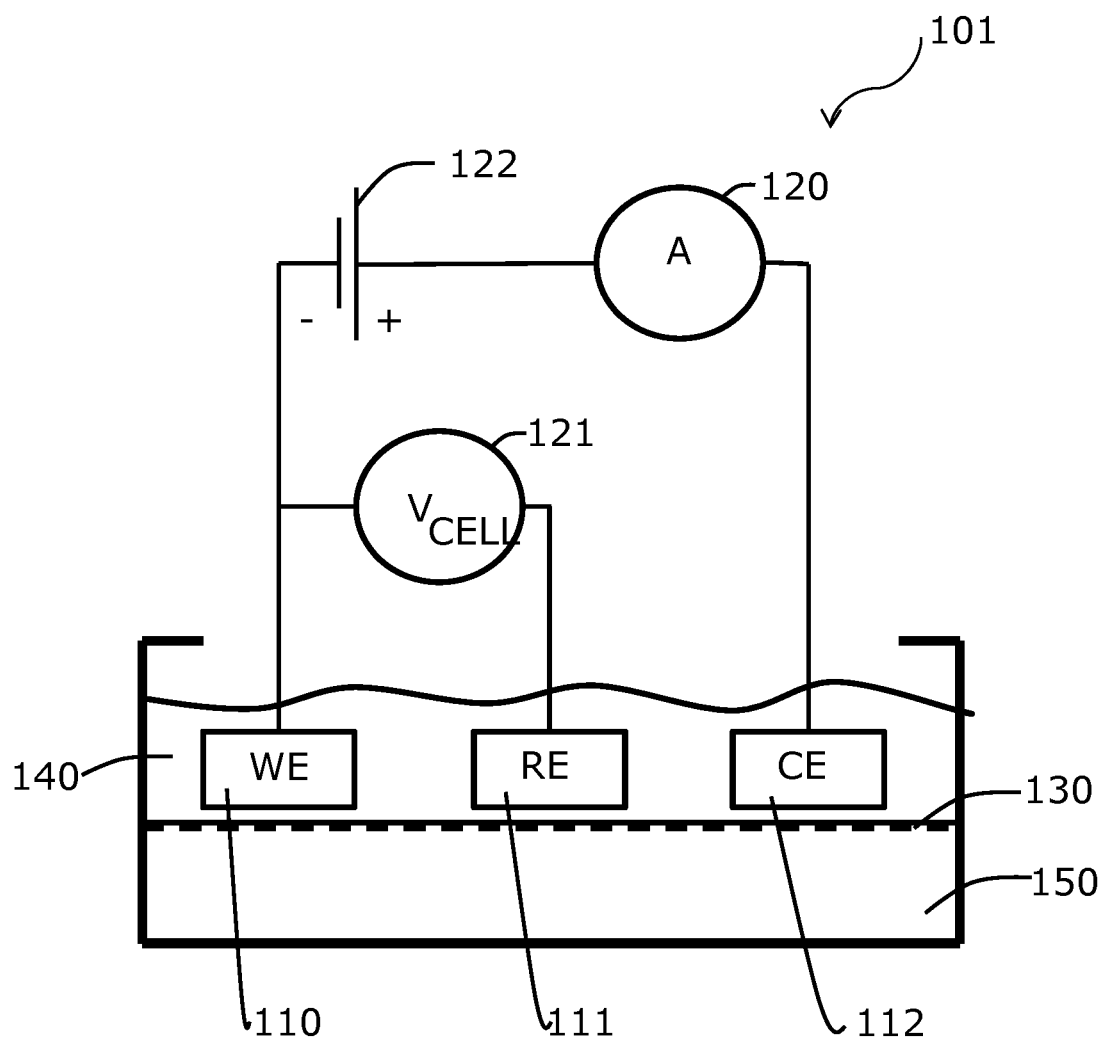
FIG. 1 is a schematic diagram of an example of an amperometric measuring system.

Reference will now be made to FIG. 1 which is a schematic diagram of a three electrode amperometric measuring system 101. An amperometric measuring system may have at least two electrodes: a working electrode (WE) 110 and a combined counter and reference electrode (CE/RE). For the three-electrode amperometric measuring system 101, the functions of the CE/RE electrode are split into two separate electrodes: the reference electrode (RE) 111 and the counter electrode (CE) 112. The example amperometric measuring system 101 also includes an ammeter 120, a voltmeter 121 and a voltage source 122 and the electrolyte solution 140.

The WE 110 is a positively charged electrode where an oxidation reaction occurs. Alternatively, the WE 110 may be a negatively charged electrode where a reduction reaction occurs. The RE 111 is typically made of Ag/AgCl and is able to maintain a stable potential, especially if no current runs through it, thus the need for a CE 112 for passing the current from the WE 110 back to the electrolyte solution 140. The electrolyte solution 140 and the sample 150 provides ionic contact between the three electrodes. The membrane 130 selectively converts the analyte to a substance that selectively is allowed to pass through from the sample 150. The voltage source 122 applies the necessary potential for maintaining the desired reduction or oxidation reaction, this is controlled by the voltmeter 121. The ammeter 120 measures the resulting current flowing through the electrical circuit, which is a measure of the free flowing electrons.

The amperometric measuring system shown in FIG. 1 is an illustrative example, and several other implementations are envisioned. For example, the amperometric measuring system could be a two electrode system as mentioned above.

The electrical current flowing through the electrode chain is proportional to the concentration of the substance being oxidized (or reduced) at the WE 110. Ideally, when knowing the proportionality constant relating the electrical current to a concentration, the concentration in any given sample can be obtained by measuring the electrical current generated by that particular sample.

To illustrate the measuring process in an amperometric measuring system, we assume that: The sample 150 contains species B, which in the membrane 130 is selectively converted to species A, which can be oxidized at the WE 110 (anode) to $A^+$; and the electrolyte 140 contains species X which is reduced at the CE 112 (cathode) to X. We assume also that the membrane 130 allows only species A to pass from the sample into the electrolyte solution 140.

As an appropriate potential is applied across the electrodes, A is oxidized at the WE 110 according to the following reaction:

$$A \rightarrow A^+ + e$$ 

The oxidation of A produces a flow of electrons. To complete the electrical circuit a reduction reaction where electrons are consumed is necessary. Therefore species X is reduced at the CE 112 according to the following reaction:

$$X + e^- \rightarrow X^-$$ 

The current flowing through the circuit is proportional to the concentration of the analyte being oxidized. The analyser can therefore automatically calculate the concentration of the analyte in the sample given species X is in excess.

The term sensor refers to a complete amperometric measuring system, as shown in FIG. 1 excluding the sample 150.

Crn is not stable in aqueous solutions, e.g. blood, where it is reversibly converted into Cr (see Scheme 1). To measure cCr, a Cr sensor is used (Crea A). To measure cCrn, a two-sensor system can be used where one sensor (Crea A) detects Cr only, and the other sensor (Crea B) detects both Cr and Crn. By means of a difference measurement it is possible to obtain the cCrn value.

Scheme 1

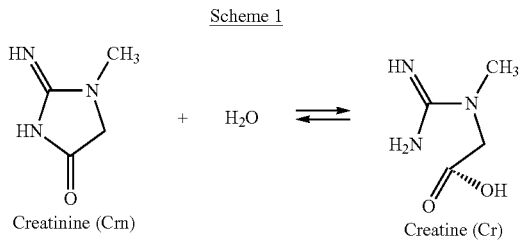

Creatinine (Crn)  Creatine (Cr)

The sensor is protected by a multilayer membrane 130 consisting of at least three functional layers, namely the outer membrane layer permeable to Crn and Cr; the middle enzyme layer, and the inner membrane layer permeable to $H_2O_2$. The multilayer membrane layer 130 may hereinafter be referred to as the enzyme layer.

In another embodiment, cCrn is determined directly with a sensor that essentially only has a sensitivity towards Crn. This may be done by applying an outer membrane that is impermeable towards Cr but permeable to Crn.

The measuring system may also contain a rinsing mechanism to clean out the system between sample measurements. For example, a rinse solution may be passed into the sample chamber to rinse out any residual substances remaining in the sample chamber or membranes. The amount of time a rinse takes is typically determined by the amount of time required to remove any residual substances. Certain residuals may take a particularly long time to remove, such as $Ca^{2+}$, which diffuses out of the enzyme layer much more slowly than other substances. In an embodiment of the proposed solution, the rinse cycles does not have to run long enough to remove all residuals, as the calibration method is adapted to take into account any residual substances that have not been removed by a rinse.

The measuring system may also contain means for measuring concentrations of modulators, like $Ca^{2+}$, $HCO_3^-$ and pH. These may be suitable for measuring the concentrations of modulator in the sample and the solution used to rinse the measuring system between uses, for example. The concentration of modulator in the rise solution may be provided with the rinse solution, so a measurement of the rinse solution may not be required.

Figure 2:
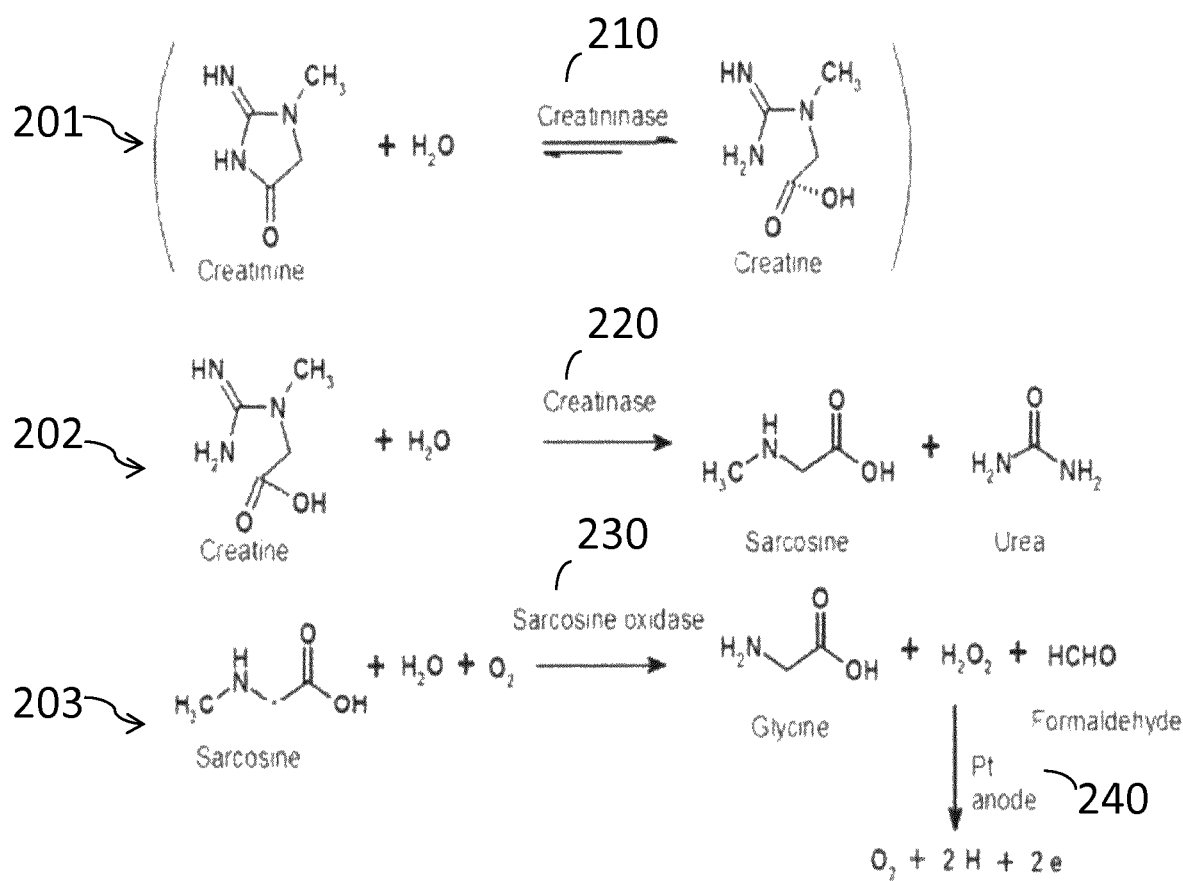
FIG. 2 is a series of diagrams illustrating the enzyme cascade for conversion of Crn to hydrogen peroxide.

FIG. 2 illustrates an example enzyme cascade for the conversion of Cr and Crn into hydrogen peroxide. In this example, enzymes creatinase (creatine amidinohydrolase) 220, sarcosine oxidase 230 and creatininase (creatinine amidohydrolase) 210 are used in the enzyme cascade. These enzymes are immobilized between the inner and outer membrane layers, while Crn and Cr molecules can diffuse across the outer membrane layer.

The Crea A sensor detects Cr by converting Cr to hydrogen peroxide in accordance with reactions 202 and 203. To achieve this conversion, the Crea A sensor uses creatine amidinohydrolase 220 and sarcosine oxidase 230. In the Crea A sensor, the enzymatic cascade changes Cr as follows:

Cr+H₂O→sarcosine+urea (creatine amidinohydrolase)

Sarcosine+H₂O+O₂→glycine+formaldehyde+
H₂O₂ (sarcosine oxidase)

The Crea B sensor contains all three enzymes creatinine amidohydrolase 210, creatine amidinohydrolase 220 and sarcosine oxidase 230, and so detects both Crn and Cr. In the enzymatic cascade Crn/Cr involves reactions 201, 202 and 203:

Crn+H₂O↔Cr (creatinine amidohydrolase)

Cr+H₂O→sarcosine+urea (creatine amidinohydrolase)

Sarcosine+H₂O+O₂→glycine+formaldehyde+
H₂O₂ (sarcosine oxidase)

For both the Crea A and the Crea B sensors the enzyme reactions lead to identical end-products, one of which is $H_2O_2$ that can diffuse across the inner membrane layer to the WE 110 (preferably platinum). By applying a sufficiently high electrical potential to the electrode chains of the Crea A and Crea B sensors, $H_2O_2$ can be oxidized at the Pt anode 240:

$H_2O_2 \rightarrow 2H^+ + O_2 + 2e^-$

To complete the electrical circuit, electrons are consumed in reduction reactions at the CE 112 thereby maintaining a charge balance between the WE 110 and the CE 112.

The oxidation of $H_2O_2$ produces an electrical current (I) proportional to the amount of $H_2O_2$, which in turn is directly related to the amount of Cr for the Crea A and the amount of Cr and Crn for the Crea B sensors according to the sensor response models:

$$I_A = Sens_{A,Cr} \cdot [Cr] = Sens_A \cdot [Cr] \qquad \text{Equation 1}$$

$$I_B = Sens_{B,Cr} \cdot [Cr] + Sens_{B,Cm} \cdot [Crn] \qquad \text{Equation 2}$$
$$= Sens_{B,Cr} \cdot \left([Cr] + \underbrace{\frac{Sens_{B,Cm}}{Sens_{B,Cr}}}_{=\alpha_B} \cdot [Crn]\right)$$
$$= Sens_B \cdot ([Cr] + \alpha_B \cdot [Crn])$$

Where $I_A$ and $I_B$ are the electrical currents produced at the Crea A and Crea B sensors respectively; $Sens_{A,Cr}$ and $Sens_{B,Cr}$ are the sensitivity constants relating current (I) to Cr concentration in the Crea A and Crea B sensors respectively and $Sens_{B,Cm}$ is the sensitivity constant relating current (I) to Crn concentration in the Crea B sensor. In the following $Sens_A$ and $Sens_B$ will be used as shorthand nomenclature for $Sens_{A,Cr}$ and $Sens_{B,Cr}$ respectively.

The proportionality constants, Sens, relating currents to concentrations are typically referred to as sensitivities. The constants are determined by calibrating the sensors. The current (signal) of each sensor is measured by ammeters 120 in the analyser. If sensor sensitivities are known, the unknown Crn concentration in a given sample is readily determined from the equations above.

The reactions illustrated in FIG. 2 can be modulated by enzyme modulators. Such enzyme modulators may be endogenous to the sample, such as $Ca^{2+}$ and $HCO_3^-$, and these enzyme modulators may inhibit the action of any of the enzymes used. The term enzyme modulator includes substances that reduce the performance of enzymes (inhibitors) or increase the performance of the enzymes.

Enzyme modulators are not limited to specific molecules, and may include other factors such as the pH or temperature of a solution or sample. It is known that factors like the pH of a solution can affect the performance of the enzyme, so factors such as pH may be referred to herein as enzyme modulators.

In the example embodiment disclosed herein, a method is provided for calibrating sensors to take into account the effects of pH, $HCO_3^-$ and $Ca^{2+}$ as modulators. However, the proposed solution is not limited to these specific modulators, and the skilled person would understand that the method can be adapted to ignore certain modulators or to include the effects of other modulators.

To model the behaviours of the modulators, in this example embodiment the sensor is considered as a 1D compartment model where the outer membrane only has diffusion resistance and no volume, and the enzyme layer only has a volume, and concentrations are the same in all of the enzyme-layer. The following derivation of the model leads to a method of calibrating a measuring system while taking into account the contributions of pH, $HCO_3^-$ and $Ca^{2+}$. However, it would be clear to the skilled person that the following derivation can be adapted to produce methods suitable for different types of modulators and sensors.

The sensor may be assumed to be in steady state with regards to Cr conversion.

As the sensor is in steady state the flux into the sensor must be equal to the conversion of Cr and the conversion must be proportional to the measured current ($I_A$)

$$Flux_{Cr} = Conversion_{Cr} \propto I_A \qquad \text{Equation 3}$$

The Flux is also equal to the permeability multiplied by the difference in concentration between the sample and the enzyme layer:

$$Flux_{Cr} = A_{sen} P_{OM}([Cr]_{sam} - [Cr]_{enz}) \qquad \text{Equation 4}$$

The term $A_{sen}$ is the area of the enzyme layer, while $P_{OM}$ represents the permeability of the outer membrane. [Cr] is the concentration of Cr in the sample, while $[Cr]_{enz}$ represents the concentration of Cr within the enzyme layer.

The conversion of Cr may be assumed to follow Michaelis-Menten kinetics with concentrations well below the Michaelis constant $K_M$ (27 mM for creatinase). The volume of the enzyme layer is the thickness ($l_{enz}$) of the enzyme layer times the area of the sensor.

$$Conversion_{Cr} = \frac{V_{max} \cdot [Cr]_{enz}}{K_M + [Cr]_{enz}} l_{enz} A_{sen} \qquad \text{Equation 5}$$

The expressions for Flux and Conversion in Equations 4 and 5 can be inserted into Equation 3 to produce Equation 6: where it is assumed that $K_M \gg [Cr]_{enz}$ $$A_{sen} P_{OM}([Cr]_{sam} - [Cr]_{enz}) = \frac{V_{max} \cdot [Cr]_{enz}}{K_M} l_{enz} A_{sen} \qquad \text{Equation 6}$$

The ideal sensor has an infinite enzyme activity and is therefore capable of reducing the concentration of Cr in the enzyme layer to 0. Therefore the flux into an ideal sensor can be expressed as:

$$Flux_{Cr,ideal} = A_{sen} P_{OM}([Cr]_{sam}) \qquad \text{Equation 7}$$

According to Eq. 1 the sensitivity of an amperometric sensor is defined as the current divided by the sample concentration.

$$Sens_A = \frac{I_A}{[Cr]_{sam}} \qquad \text{Equation 8}$$

The ratio between the sensitivity and the ideal sensitivity can be particularly useful for calibrating sensors. Therefore, the expression for the current in Equation 3 can be inserted into the sensor formula in Equation 8 to provide an expression for this ratio of sensitivities:

$$\frac{Sens_A}{Sens_{A,ideal}} = \frac{\frac{I_A}{[Cr]_{sam}}}{\frac{I_{A,ideal}}{[Cr]_{sam}}} = \frac{I_A}{I_{A,ideal}} = \frac{Flux_{Cr}}{Flux_{Cr,ideal}} \qquad \text{Equation 9}$$

The expressions for Flux and ideal Flux from Equations 4 and 7 can be substituted into Equation 9 and simplified into Equation 10:

$$\frac{Sens_A}{Sens_{A,ideal}} =$$

$$\frac{Flux_{Cr}}{Flux_{Cr,ideal}} = \frac{A_{sen} P_{OM}([Cr]_{sam} - [Cr]_{enz})}{A_{sen} P_{OM}([Cr]_{sam})} = 1 - \frac{[Cr]_{enz}}{[Cr]_{sam}} \qquad \text{Equation 10}$$

Equation 6 can be rewritten to be an expression for the Cr concentration in the enzyme layer ($[Cr]_{enz}$):

$$[Cr]_{enz} = \frac{P_{OM}[Cr]_{sam}}{\left(\frac{V_{max} \cdot l_{enz}}{K_M} + P_{OM}\right)} \qquad \text{Equation 11}$$

The expression for Cr concentration in the enzyme layer in Equation 11 can be substituted into Equation 10 to provide an expression for the ratio of sensor sensitivity and ideal sensitivity:

$$\frac{Sens_A}{Sens_{A,ideal}} = 1 - \frac{1}{\left(\frac{V_{max} l_{enz}}{K_M P_{OM}} + 1\right)} \qquad \text{Equation 12}$$

$V_{max}$ over $K_M$ can be expressed in the form of units:

$$\frac{V_{max}}{K_M} = \frac{U}{A_{sen} l_{enz}} \cdot \alpha(t) \cdot mod(pH_{enz}, [HCO_3^-]_{enz}, [Ca^{2+}]_{enz}) \qquad \text{Equation 13}$$

Where U is the amount of units dispensed on the sensor (unit mol/sec). U can be divided by the volume of the enzyme layer, namely ($A_{sen} l_{enz}$). The $\alpha(t)$ term represents the remaining activity at the time t and can range in value from 0 to 1. The degree of modulation 'mod' provides an estimate for how much the enzyme is modulated in the given pH, and $HCO_3^-$ and $Ca^{2+}$ concentration. The value range for the mod can be between 0 and 1. This function can only be predicted empirically.

Inserting the expression for $$\frac{V_{max}}{K_M}$$

in Equation 13 into Equation 12 yields the final expression for the ratio of sensitivities:

$$\frac{Sens_A}{Sens_{A,ideal}} = \quad \text{Equation 14}$$

$$1 - \frac{1}{\left(\frac{U}{A_{sen}} \cdot \alpha(t) \cdot \text{mod}(pH_{enz}, [HCO_3^-]_{enz}, [Ca^{2+}]_{enz}) \cdot \frac{1}{P_{OM}} + 1\right)}$$

Equation 14 only applies for a two-enzyme sensor (Crea A) in which Crn is not considered. If the sensor contains excess creatininase enzyme activity, some of the Cr will immediately be converted into Crn in the enzyme layer. To take into account this possibility, Equation 14 can be modified to consider the total flux of Cr as well as Crn. Assuming the sample only contains Cr (as many calibration solutions do) results in the following modification of Equation 14:

$$\text{Flux}_{Cr+Crn} = A_{sen}P_{OM,Cr}([Cr]_{sam} - [Cr])_{enz}) + A_{sen}P_{OM,Crn}(-[Crn]_{enz}) \quad \text{Equation 14A}$$

Equation 14A can be reduced by introducing 13, the equilibrium ratio between Crn and Cr, and the ratio between the permeabilities (assumed to be equal to the ratio between the diffusion coefficients):

$$\text{Flux}_{Cr+Crn} = \quad \text{Equation 14B}$$

$$A_{sen}P_{OM,Cr}\left([Cr]_{sam} - \left(1 + \frac{[Crn]_{enz}}{[Cr]_{enz}} \frac{P_{OM,Crn}}{P_{OM,Cr}}\right)[Cr]_{enz}\right)$$

$$\text{Flux}_{Cr+Crn} = A_{sen}P_{OM,Cr}\left([Cr]_{sam} - \left(1 + \beta\frac{D_{cm}}{D_{Cr}}\right)[Cr]_{enz}\right)$$

Where $\beta = \frac{[Crn]_{enz}}{[Cr]_{enz}}$

Using Flux defined in Equation 14B rather than Equation 4 would result in a modified version of Equation 14 for the three-enzyme sensor (Crea B):

$$\frac{Sens_B}{Sens_{B,ideal}} = \quad \text{Equation 14C}$$

$$1 - \frac{1}{\left(\frac{U}{A_{sen}} \cdot \alpha(t) \cdot \text{mod}(pH_{enz}, [HCO_3^-]_{enz}, [Ca^{2+}]_{enz}) \frac{1}{\left(1 + \beta\frac{D_{cm}}{D_{Cr}}\right)P_{OM}} + 1\right)}$$

where the sensitivity $Sens_B$ of the Crea B sensor is defined according to Eq. 2 as the current divided by the sample concentrations of Cr and Crn, where the latter concentration is multiplied by the ratio $\alpha_B$ between the sensor sensitivities towards Cr and Crn.

$$Sens_B = \frac{I_B}{[Cr]_{sam} + \alpha_B[Crn]_{sam}}$$

The expression for a three-enzyme sensor (Crea B) (Equation 14C) is similar to the expression for a two-enzyme sensor (Crea A) (Equation 14), but the three-enzyme sensor formula includes the factor $$\frac{1}{\left(1 + \beta\frac{D_{cm}}{D_{Cr}}\right)}.$$

When $\beta = 0.7$ and $$\frac{D_{cm}}{D_{Cr}}$$

is roughly 1.25, the enzyme activity in a three-enzyme sensor is divided by a factor of roughly 2, compared to a two-enzyme sensor.

To establish a correction for the modulated sensor, a functional form of the mod function needs to be determined. To do this, mod is isolated from Equation 14C:

$$\frac{Sens_B}{Sens_{B,ideal}} = \quad \text{Equation 15}$$

$$1 - \frac{1}{\left(\frac{U}{A_{sen}} \cdot \alpha(t) \cdot \text{mod}(pH_{enz}, [HCO_3^-]_{enz}, [Ca^{2+}]_{enz}) \cdot \frac{1}{\left(1 + \beta\frac{D_{cm}}{D_{Cr}}\right)P_{OM}} + 1\right)}$$

$$\frac{U}{A_{sen}} \cdot \alpha(t) \cdot \text{mod}(pH_{enz}, [HCO_3^-]_{Enz}, [Ca^{2+}]_{enz}) \cdot \frac{1}{\left(1 + \beta\frac{D_{cm}}{D_{Cr}}\right)P_{OM}} +$$

$$1 = \frac{1}{1 - \frac{Sens_B}{Sens_{B,ideal}}} \text{mod}(pH_{enz}, [HCO_3^-]_{enz}, [Ca^{2+}]_{enz}) =$$

$$\left(\frac{1}{1 - \frac{Sens_B}{Sens_{B,ideal}}} - 1\right) \frac{\left(1 + \beta\frac{D_{cm}}{D_{Cr}}\right)P_{OM}}{\frac{U}{A_{sen}}\alpha(t)}$$

If a series with varying pH, $HCO_3^-$ and $Ca^{2+}$ is aspirated on the same sensor with a short time frame, the right term can be considered to be constant and can be replaced by the constant $C_1$:

$$\text{mod}(pH_{enz}, [HCO_3^-]_{enz}, [Ca^{2+}]_{enz}) = \quad \text{Equation 16}$$

$$\left(\frac{1}{1 - \frac{Sens_B(pH_{enz}, [HCO_3^-]_{enz}, [Ca^{2+}]_{enz})}{Sens_{B,ideal}}} - 1\right)C_1$$

From this term one can measure mod as a function of pH and $HCO_3^-$ in the sample. If we assume that the modulation consists of three separate functions we get the following term:

$$\text{mod}(pH_{enz}, [HCO_3^-]_{enz}, [Ca^{2+}]_{enz}) = \text{mod}(pH_{enz}) \cdot \text{mod}([HCO_3^-]_{enz}) \cdot \text{mod}([Ca^{2+}]_{enz}) \quad \text{Equation 17}$$

$HCO_3^-$ is assumed to be a competitive inhibitor thereby altering the $K_M$ term in Michaelis-Menten kinetics by a factor as illustrated in Equation 18:

$$Conversion_{Cr} = \frac{V_{max}[Cr]_{enz}}{K'_M} l_{enz} A_{sen} \quad \text{Equation 18}$$

where $K'_M = K_M(1 + [HCO_3^-]_{enz}/K_i)$ $K_i$ in Equation 18 is the dissociation constant. The form of the $\text{mod}([HCO_3^-]_{enz})$ term in Equation 17 can be estimated by inserting Equation 18 into Equation 13:

$$\text{mod}(pH_{enz}, [HCO_3^-]_{enz}, [Ca^{2+}]_{enz}) = \quad \text{Equation 19}$$
$$\text{mod}(pH_{enz}) \frac{1}{(1 + [HCO_3^-]_{enz}/K_i)} \cdot \text{mod}([Ca^{2+}]_{enz})$$

As $Ca^{2+}$ also contributes to the inhibition of the enzyme, it should also be factored into the modulation factor of $HCO_3^-$, i.e., $$\text{mod}(pH_{enz}, [HCO_3^-]_{enz}, [Ca^{2+}]_{enz}) = \text{mod}(pH_{enz}) \cdot \text{mod}([HCO_3^-]_{enz}, [Ca^{2+}]_{enz}).$$

Solving the system for the reaction between $Ca^{2+}$, $HCO_3^-$ (bicarbonate) and the enzyme (Enz-Bi denotes enzyme inhibited by one $HCO_3^-$; Enz-Bi—Ca denotes enzyme inhibited by one $HCO_3^-$ and one $Ca^{2+}$):

$$k_1 = \frac{[Enz]_{enz}[HCO_3^-]_{enz}}{[Enz\text{-}Bi]_{enz}}$$

$$k_2 = \frac{[Enz]_{enz}[HCO_3^-]_{enz}[Ca^{2+}]_{enz}}{[Enz\text{-}Bi\text{-}Ca]_{enz}}$$

The mass balance for the total amount of enzyme ($cEnz_{total}$) is given by:

$$[Enz\text{-}Bi\text{—}Ca]_{enz} + [Enz\text{-}Bi]_{enz} + [Enz]_{enz} = cEnz_{total}$$

Insertion and isolation of [Enz] in the equations above yields:

$$\frac{[Enz]}{cEnz_{total}} = \frac{1}{1 + \frac{[HCO_3^-]_{enz}}{k_1} + \frac{[HCO_3^-]_{enz}[Ca^{2+}]_{enz}}{k_2}}$$

From this equation it can be seen that a more accurate form for Equation 19 would be:

$$\text{mod}(pH_{enz}, [HCO_3^-]_{enz}, [Ca^{2+}]_{enz}) = \quad \text{Equation 20}$$
$$\text{mod}(pH_{enz}) \cdot \text{mod}([HCO_3^-]_{enz}, [Ca^{2+}]_{enz}) =$$
$$\text{mod}(pH_{enz}) \cdot \frac{1}{\left(1 + \frac{[HCO_3^-]_{enz}}{k_1} + \frac{[HCO_3^-]_{enz}[Ca^{2+}]_{enz}}{k_2}\right)}$$

Next, the effect of pH (mod(pH)) can be estimated, but as pH is not a simple inhibition, the same method cannot be used. Histidine (His232) plays a role in the active site of the creatinase, and the pH dependency may be determined by the charge of this histidine group. Since the enzyme activity increases with increasing pH one can assume that the uncharged histidine group is the one with enzyme activity. Therefore, assuming that histidine follows ordinary buffer thermodynamics, the following expression for pH can be estimated:

$$pH_{enz} = pK_{a,His} + \log\left(\frac{[Enz\text{-}His]}{[Enz\text{-}HisH^+]}\right) \quad \text{Equation 21}$$

If one substitutes the charged histidine with the following expression:

$$[Enz\text{-}HisH^+] = cEnz_{total} - [Enz\text{-}His]$$

Then if one isolates the uncharged histidine, the resulting expression would be:

$$[Enz\text{-}His] = cEnz_{total} \frac{K_a}{10^{(-pH_{enz})} + K_a}$$

Assuming that it is only the enzymes with uncharged His232 that are active, the final modulation term can be given as:

$$\text{mod}([pH]_{enz}, [HCO_3^-]_{enz}, [Ca^{2+}]_{enz}) = cEnz_{total} \quad \text{Equation 22}$$
$$\frac{K_a}{10^{(-pH_{enz})} + K_a} \left(1 + \frac{[HCO_3^-]_{enz}}{k_1} + \frac{[HCO_3^-]_{enz}[Ca^{2+}]_{enz}}{k_2}\right)$$

By normalizing Equation 22 with respect to the total concentration $cEnz_{total}$, as this term is included as a part of $C_1$ in Equation 16 the range of modulation values can be limited to range between 0 and 1:

$$\text{mod}([pH]_{enz}, [HCO_3^-]_{enz}, [Ca^{2+}]_{enz}) = \quad \text{Equation 23}$$
$$\frac{K_a}{10^{(-pH_{enz})} + K_a} \cdot \frac{1}{\left(1 + \frac{[HCO_3^-]_{enz}}{k_1} + \frac{[HCO_3^-]_{enz}[Ca^{2+}]_{enz}}{k_2}\right)}$$

The value for $K_a$ can be determined in a number of ways. For example, by fitting Equation 23 to an example set of real data, it was determined that $K_a$ had a value of $10^{-7.9}$ for that example set.

The model described above assumes the systems are in a steady state. However, while the system is measuring, it will not necessarily be in steady state, particularly after a short period of time after measurements have started. In the example provided, this short time period will be taken to be 17 seconds, although shorter or longer times may be envisioned.

$HCO_3^-$ and pH typically have a fast time constant, therefore the sensors are typically equilibrated after a short rinse before the next sample is aspirated. Therefore, when determining the non-steady state amount of $HCO_3^-$ and pH levels within the enzyme layer, it is a fair approximation to only examine the effect from the current sample, rather than from any residual amounts from a previous measurement.

However, $Ca^{2+}$ has a much higher time constant and sensors are likely to "remember" previous samples with high $Ca^{2+}$. For example, residual $Ca^{2+}$ may still be present in an enzyme layer after rinsing for a short period of time, as short rinses do not give sufficient time for $Ca^{2+}$ to diffuse out into the rinse solution. While setting a longer rinse cycle may help to reduce the amount of residual $Ca^{2+}$, this would increase the time between samples, thereby reducing the rate of sample taking. Performing a complete cycle may result in periods of 3 minutes or more between measurements, while it would be preferable to reduce this to 1 minute or less. Therefore, instead of performing a full rinse cycle, the proposed solution performs a partial rinse and then factors in the amount of $Ca^{2+}$ (or any other modulator) remaining in the system from the previous sample.

Estimating the Concentration of $HCO_3^-$ in the Enzyme Layer

One can estimate the sample induced change in $HCO_3^-$ concentration in the enzyme layer after 17 seconds by mass balance of the two main contributors: $HCO_3^-$ itself and $CO_2$:

$$[HCO_3^-]_{enz} = \qquad\qquad \text{Equation 24}$$
$$[HCO_3^-]_{enz,t=0s} + \frac{\text{Flux}_{HCO_3^-,t=0\to17s} + \text{Flux}_{CO_2,t=0\to17s}}{A_{sen}l_{enz}}$$

The flux into the sensor can be approximated by a simple linear model, where two constants $C_1$ and $C_2$ are introduced (that also contain t=17 seconds, $A_{sen}$, $P_{OM}$ and $l_{enz}$):

$$\text{Flux}_{HCO_3^-,t=0\to17\,s} = {}_1A_{sen}l_{enz}([HCO_3^-]_{sam} - [HCO_3^-]_{enz,t=0\,s})\ \text{Flux}_{CO_2,t=0\to17\,s} = C_2 A_{sen}l_{enz}([CO_2]_{sam}[CO_2]_{enz,t=0\,s})$$

$$[HCO_3^-]_{enz} \approx [HCO_3^-]_{Rinse} + C1_{HCO3}([HCO_3^-]_{sam} - [HCO_3^-]_{Rinse}) + C2_{CO2}([CO_2]_{sam} - [CO_2]_{Rinse}) \qquad \text{Equation 25}$$

As the $H_2O_2$ measured in a Crn sensor will have been generated over the whole 17 seconds that the sensor has been measuring, an approximation of the average $HCO_3^-$ over the 17 seconds would be useful to determine. The expression for concentration at 17 s in Equation 25 should be sufficiently accurate for substituting into Equation 23 when determining the degree of modulation (mod) for a sample.

Values for the two constant values $C1_{HCO3}$ and $C2_{CO2}$ can be determined through various means. For example, optimization through standard performance tests may show that the optimum values for the two constants may be:

$$C1_{HCO3} = 0.5$$
$$C2_{CO2} = 0.05 \frac{mM}{mmHg}$$

Estimating pH in the Enzyme Layer

As pH is defined by a logarithmic function, the non-steady state modelling requires a number of extra steps. The contributors to the pH may include both mobile and immobilized buffers. Where one mobile buffer mBuf is assumed to be the main buffering agent with conjugate acid $mBuf_A$ and base $mBuf_B$ species, the sample induced pH change in the enzyme layer afters 17 s can be expressed as:

$$pH_{enz} = pK_{a,mBuf} - \log\left(\frac{[mBuf_A]_{enz}}{[mBuf_B]_{enz}}\right)$$

$pK_a$ for buffers can take a number of values, but here one with a $pK_a$ of 7.0 is used. Assuming a fixed amount of immobile buffer capacity from the enzymes with the same pKa as the mobile buffer, the equation for pH becomes:

$$pH = pK_{a,mBuf} - \log\left(\frac{[mBuf_A]_{enz} + [imBuf_A]_{enz}}{[mBuf_B]_{enz} + [imBuf_B]_{enz}}\right)$$

As pKa of most species in rinse and samples is significantly higher or lower than 7, the only relevant mechanisms for changing pH in the sensor are $CO_2$ converted into $H^+$ and $HCO_3^-$. This can be reflected in the pH equation as follows:

$$pH_{enz} = pK_{a,mBuf} - \log\left(\frac{[mBuf_A]_{enz} + [imBuf_A]_{enz} + \Delta[H^+]_{enz,CO_2}}{[mBuf_B]_{enz} + [imBuf_B]_{enz} - \Delta[H^+]_{enz,CO_2}}\right)$$

The amount of $H^+$ generated from $CO_2$ can be approximated by the following equation, where the $CO_2$ constant ($C2_{CO2}$) is reused from Equation 25:

$$\Delta[H^+]_{enz,CO_2} = \qquad\qquad \text{Equation 26}$$
$$\frac{\text{Flux}_{CO_2,t=0\to17s}}{A_{sen}l_{enz}} = C2_{CO2}([CO_2]_{sam} - [CO_2]_{Rinse})$$

Another indirect method for pH changes is loss of mobile buffer during measuring (and possibly a gain during calibration):

$$[mBuf_A]_{enz} \approx [mBuf_A]_{Rinse} + C_3([mBuf_A]_{sam} - [mBuf_A]_{Rinse})\ [mBuf_B]_{enz} \approx [mBuf_B]_{Rinse} + C_3([mBuf_B]_{sam} - [mBuf_B]_{Rinse})$$

These terms can be inserted into the pH equation above to result in:

$$pH_{enz} = pK_{a,mBuf} - \log\left(\frac{\begin{array}{l}[mBuf_A]_{Rinse} + C_3([mBuf_A]_{sam} - [mBuf_A]_{Rinse}) +\\ [imBuf_A]_{enz} + C2_{CO2}([CO_2]_{sam} - [CO_2]_{Rinse})\end{array}}{\begin{array}{l}[mBuf_B]_{Rinse} + C_3([mBuf_B]_{sam} - [mBuf_B]_{Rinse}) +\\ [imBuf_B]_{enz} - C2_{CO2}([CO_2]_{sam} - [CO_2]_{Rinse})\end{array}}\right)$$

The contribution from mobile buffer diffusion is typically insignificant and the amount of buffer from the enzyme layer can be ignored, hence the equation can be simplified to Equation 27:

$$pH_{Enz} = pK_{a,mBuf} - \qquad\qquad \text{Equation 27}$$
$$\log\left(\frac{[mBuf_A]_{Rinse} + C2_{CO2}([CO_2]_{sam} - [CO_2]_{Rinse})}{[mBuf_B]_{Rinse} - C2_{CO2}([CO_2]_{sam} - [CO_2]_{Rinse})}\right)$$

This expression for pH can be used in Equation 23 when determining the degree of modulation (mod) for a sample.

Estimating the Concentration of $Ca^{2+}$ in the Enzyme Layer $Ca^{2+}$ has a much slower time constant than pH and $HCO_3^+$, and therefore after a short rinse there may still be residual $Ca^{2+}$ remaining. To allow for short rinse times, the proposed solution tracks the history of the $Ca^{2+}$ concentration in the measuring system.

Diffusion in and out of compartments (such as the enzyme layer) can be modelled by an exponential decay function. Therefore, the concentration in the enzyme layer immediately before a new sample is aspirated can be expressed as:

$$[Ca^{2+}]_{enz,Before\ new\ asp.} = \qquad \text{Equation 28}$$

$$[Ca^{2+}]_{Rinse} + ([Ca^{2+}]_{enz,After\ last\ asp.} - [Ca^{2+}]_{Rinse})e^{\frac{-\Delta t}{\tau}}$$

Where $\Delta t$ is the time from last sample until the new sample is aspirated; $[Ca^{2+}]_{enz,After\ last\ asp.}$ is the $Ca^{2+}$ concentration in the enzyme layer at the end of the last sample; and $\tau$ is the time constant specific for the sensor construction.

The concentration in the enzyme layer follows the same function while exposed to the sample. In this example the exposure time is taken to be 20 seconds.

$$[Ca^{2+}]_{enz,After\ new\ asp.} = \qquad \text{Equation 29}$$

$$[Ca^{2+}]_{sam} + ([Ca^{2+}]_{enz,Before\ new\ asp.} - [Ca^{2+}]_{sam})e^{\frac{-20}{\tau}}$$

The expression for $c[Ca^{2+}]_{enz,Before\ new\ asp.}$ in Equation 28 can be substituted into Equation 29 to form a single equation that shows the correlation between the time since last sample, the concentration in the enzyme layer after the last sample and the concentration of the current sample:

$$[Ca^{2+}]_{enz,After\ new\ asp.} = [Ca^{2+}]_{sam} + \qquad \text{Equation 30}$$

$$\left([Ca^{2+}]_{Rinse} + ([Ca^{2+}]_{enz,After\ last\ asp.} - [Ca^{2+}]_{Rinse})e^{\frac{-\Delta t}{\tau}} - [Ca^{2+}]_{sam}\right)e^{\frac{-20}{\tau}}$$

Equation 30 can be used to track the $Ca^{2+}$ concentration as a function of time and samples. This equation may be further modified for estimating the $Ca^{2+}$ concentration used in the modulation function, to take into account the fact that a measurement is only performed for 17 seconds, whereas the estimate above is for 20 seconds. Therefore, the equation can be optimized by defining the $Ca^{2+}$ concentration in the middle of the 17 second measurement (8.5 seconds):

$$[Ca^{2+}]_{enz} = [Ca^{2+}]_{sam} + \qquad \text{Equation 31}$$

$$\left([Ca^{2+}]_{Rinse} + ([Ca^{2+}]_{enz,After\ last\ asp.} - [Ca^{2+}]_{Rinse})e^{\frac{-\Delta t}{\tau}} - [Ca^{2+}]_{sam}\right)e^{\frac{-8.5}{\tau}}$$

Equation 30 is used to track the $Ca^{2+}$ concentration over time, while Equation 31 may be more suitable for substituting into the modulator function in Equation 23.

Now that expressions for determining mod $([pH]_{enz}, [HCO_3^-]_{enz}, [Ca_{2+}]_{enz})$ have been established, the remaining terms of Equation 14C should be evaluated. Terms that are not sample dependent may be isolated into a single variable phi ($\varphi$) that can be determined by calibration:

$$\frac{Sens_B}{Sens_{B,ideal}} = \qquad \text{Equation 32}$$

$$1 - \frac{1}{\left(\dfrac{\dfrac{U}{A_{sen}}\alpha(t)\text{mod}(pH_{enz}, [HCO_3^-]_{enz}, [Ca^{2+}]_{enz})}{\left(1 + \beta\dfrac{D_{cm}}{D_{Cr}}\right)P_{OM}} + 1\right)}$$

$$\varphi_B = \frac{\dfrac{U}{A_{sen}}\alpha(t)}{\left(1 + \beta\dfrac{D_{cm}}{D_{Cr}}\right)P_{OM,Cr}} =$$

$$\frac{\dfrac{1}{1 - \dfrac{Sens_B}{Sens_{B,ideal}}} - 1}{\text{mod}([pH]_{enz}, [HCO_3^-]_{enz}, [Ca^{2+}]_{enz})}$$

$\varphi$ is a dimensionless constant that is an expression of the ratio between enzyme activity and the permeability of the sensor. It can be determined each time a calibration is performed by evaluating the right side of Equation 32.

The sensitivity of a sample needs to be corrected with the following term:

$$\frac{\dfrac{Sens_{B,sam}}{Sens_{B,ideal}}}{\dfrac{Sens_{B,Cal}}{Sens_{B,ideal}}} = \frac{1 - \dfrac{1}{\varphi_B \cdot \text{mod}(pH_{enz}, [HCO_3^-]_{enz}, [Ca^{2+}]_{enz})_{sam} + 1}}{1 - \dfrac{1}{\varphi_B \cdot \text{mod}(pH_{enz}, [HCO_3^-]_{enz}, [Ca^{2+}]_{enz})_{Cal} + 1}} \qquad \text{Equation 33}$$

$$Sens_{B,sam} = Sens_{B,Cal}\frac{1 - \dfrac{1}{\varphi_B \cdot \text{mod}_{sam} + 1}}{1 - \dfrac{1}{\varphi_B \cdot \text{mod}_{Cal} + 1}}$$

The indices on mod indicate that the modulation function is evaluated for the aspiration of a sample or a calibration solution. If the Crn/Cr correction term needs to be implemented then $\varphi$ may be corrected by finding an analytic expression for $P_{OM}$.

In the example embodiment provided, sensitivities for two calibration solutions ($Sens_{B,Cal2}$ and $Sens_{B,Cal3}$) can be determined, but a value for $Sens_{B,ideal}$ is missing. An expression for $\varphi$ with missing $Sens_{B,ideal}$ data, but obtainable Cal2 and Cal3 data can be found as:

$$\frac{\dfrac{Sens_{B,Cal3}}{Sens_{B,ideal}}}{\dfrac{Sens_{B,Cal2}}{Sens_{B,ideal}}} = \frac{Sens_{B,Cal3}}{Sens_{B,Cal2}} = \frac{1 - \dfrac{1}{\varphi \cdot \text{mod}_{Cal3} + 1}}{1 - \dfrac{1}{\varphi \cdot \text{mod}_{Cal2} + 1}} \qquad \text{Equation 34}$$

$$\varphi = \frac{1}{\text{mod}_{Cal3} \cdot \left(\dfrac{Sens_{B,Cal2}}{Sens_{B,Cal3}} - 1\right)} + \frac{1}{\text{mod}_{Cal2} \cdot \left(\dfrac{Sens_{B,Cal3}}{Sens_{B,Cal2}} - 1\right)}$$

The above calibration model derived for Steady state data (Equations 33 and 34) combined with the non-steady state modulator function (Equations 33, 35, 37 and 41) is suitable for correcting sensors even though measurements are not necessarily taken in steady state.

The derivation of the calibration model described can be adapted by the skilled person to accommodate for different configurations, such as differences in enzymes, modulators, timings and numbers of calibration solutions. Using the derived calibration model, it is possible for the skilled person to perform accurate calibrations that take account of modulators, while keeping the time between sample measurements relatively short.

Figure 3:
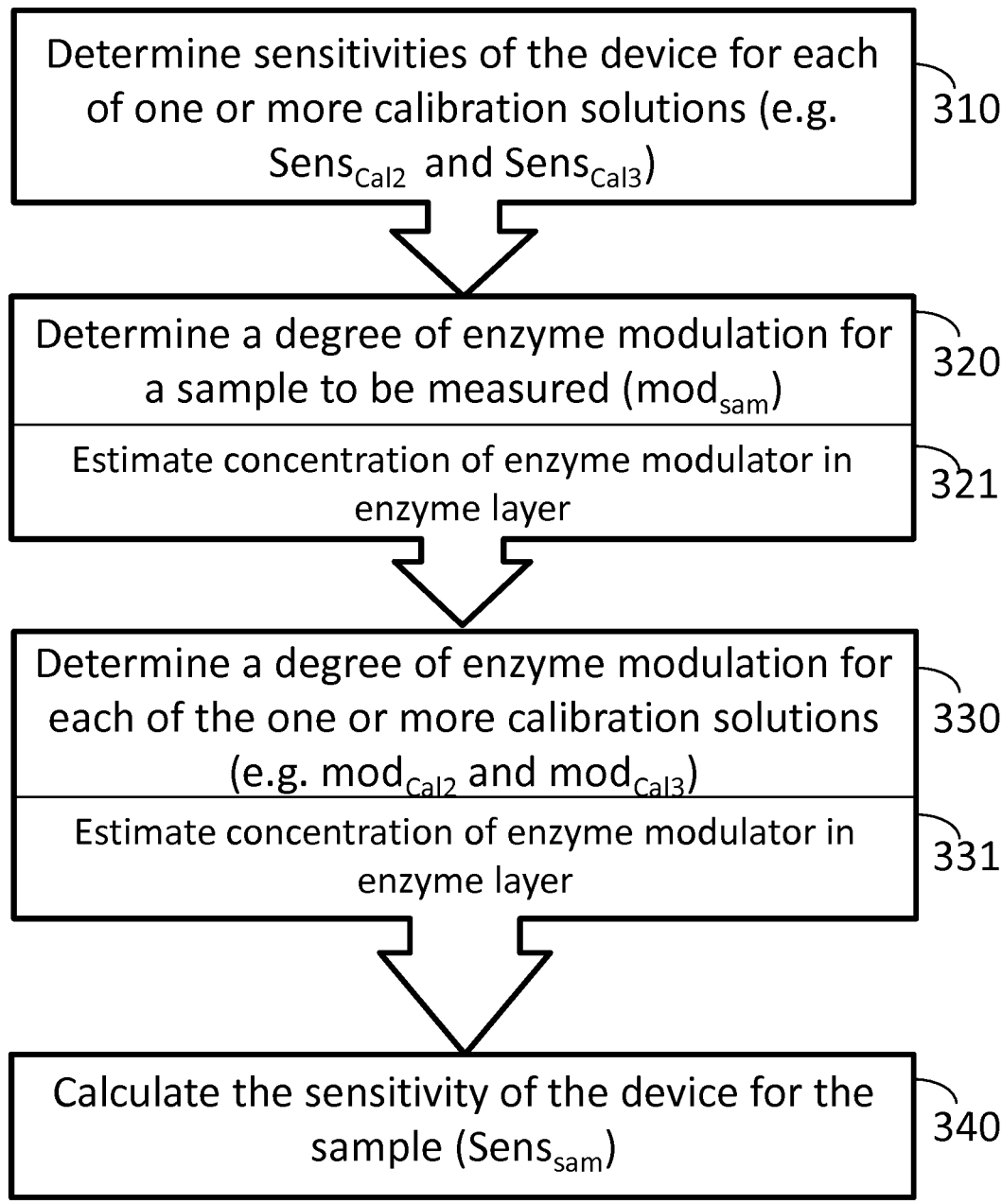
FIG. 3 is a flowchart outlining the steps of the proposed method.

FIG. 3 outlines the steps for carrying out an example embodiment of the proposed method. The proposed method is not limited to the ordering of the steps shown in FIG. 3, nor is the method envisioned to be solely limited to this example embodiment provided.

At step 310, sensitivities of the device for each of the one or more calibration solutions are determined. Said determining of sensitivities may involve calculating the ratio between an amperometer output (current, I) and the known concentration of Cr or Crn of the calibration solution, as well as the ratio $\alpha_B$ between the sensitivities of the Crea B sensor. In some embodiments, the concentrations of Cr or Crn of the calibration solutions need to be determined or adjusted from an initial concentration, while in other embodiments the concentrations are provided as data accompanying the calibration solutions.

For example, the sensitivity of one calibration solution Cal2 can be given by:

$$Sens_{A,Cal2} = \frac{I_{A,Cal2}}{[Cr]_{Cal2}}$$

$$Sens_{B,Cal2} = \frac{I_{B,Cal2}}{[Cr]_{Cal2} + \alpha_B \cdot [Crn]_{Cal2}}$$

Similarly, the sensitivity for another calibration solution Cal3 can be given by:

$$Sens_{A,Cal3} = \frac{I_{A,Cal3}}{[Cr]_{Cal3}}$$

$$Sens_{B,Cal3} = \frac{I_{B,Cal3}}{[Cr]_{Cal3} + \alpha_B \cdot [Crn]_{Cal3}}$$

It may be advantageous to use two calibration solutions where different amounts of enzyme modulators are provided in the calibration solutions, effectively providing two data points for determining the relationship between enzyme modulators and sensitivity. Providing more than two calibration solutions of different amounts of enzyme modulators may lead to more accurate results. One calibration solution may be chosen to have very low or no enzyme modulators, while another calibration solution may be chosen to have enzyme modulators around the same order of magnitude as the expected amount of enzyme modulators in samples. In this way, the second calibration solution a sensitivity close to the expected samples, while the first calibration solution provides sensitivities sufficiently distant from the second calibration solution to provide a good measure of the relationship between enzyme modulation and sensitivity.

At step 320, the degree of enzyme modulation is determined for the sample to be measured. This degree of enzyme modulation is a measure of how much enzyme activity is modulated in a given sample. For example, where a $HCO_3^-$ concentration ($[HCO_3^-]$), $Ca^{2+}$ concentration ($[Ca^{2+}]$), and higher-than-optimum alkalinity (pH) are present, these may inhibit the enzyme activity by a certain percentage given by the degree of modulation.

The modulation function for the measured sample can be determined by:

$$mod_{Sam} = \frac{K_a}{10^{(-pH_{enz})} + K_a} \frac{1}{\left(1 + \frac{[HCO_3^-]_{enz}}{k_1} + \frac{[HCO_3^-]_{enz}[Ca^{2+}]_{enz}}{k_2}\right)}$$

To determine this modulation function, values for $pH_{enz}$, $[HCO_3^-]_{enz}$, and $[Ca^{2+}]_{meas}$ need to be evaluated. A value for $pH_{enz}$ may be determined using Equation 27, namely $$pH_{enz} = pK_{a,mBuf} - \log\left(\frac{[mBuf_A]_{Rinse} + C2_{CO2}([CO_2]_{sam} - [CO_2]_{Rinse})}{[mBuf_B]_{Rinse} - C2_{CO2}([CO_2]_{sam} - [CO_2]_{Rinse})}\right)$$

A value for the $HCO_3^-$ concentration may be determined using Equation 25, namely $$[HCO_3^-]_{enz} \approx [HCO_3^-]_{Rinse} + C1_{HCO3}([HCO_3^-]_{sam} - [HCO_3^-]_{Rinse}) + C2_{CO2}([CO_2]_{sam} - [CO_2]_{Rinse})$$

A value for $Ca^{2+}$ concentration can be determined using Equation 31 where the concentrations of $Ca^{2+}$ in previous samples as well as time are taken into account so as to factor in the amount of enzyme modulator in the enzyme layer (321):

$$[Ca^{2+}]_{enz} = [Ca^{2+}]_{sam} + \left(([Ca^{2+}]_{Rinse} + ([Ca^{2+}]_{enz, After\ last\ asp.} - [Ca^{2+}]_{Rinse})e^{\frac{-\Delta t}{\tau}} - [Ca^{2+}]_{sam}\right)e^{\frac{-8.5}{\tau}}$$

With values of $pH_{enz}$, $[HCO_3^-]_{enz}$ and $[Ca^{2+}]_{enz}$ evaluated, the mod function for the sample can be determined. This may be repeated for each sample measured At step 330, the modulation functions $mod_{Cal2}$ and $mod_{Cal3}$ for calibration solutions Cal2 and Cal3 are determined using the same methodology as used for the sample. First the values for $pH_{enz}$, $[HCO_3^-]_{enz}$ and $[Ca^{2+}]_{enz}$ need to be evaluated for each calibration solution whereafter the modulation functions can be calculated. A value for $pH_{enz}$ may be determined for Cal2 and Cal3 calibration solutions using Equation 27:

$$pH_{enz,Cal2} = pK_{a,mBuf} - \log\left(\frac{[mBuf_A]_{Rinse} + C2_{CO2}([CO_2]_{Cal2} - [CO_2]_{Rinse})}{[mBuf_B]_{Rinse} - C2_{CO2}([CO_2]_{Cal2} - [CO_2]_{Rinse})}\right)$$

$$pH_{enz,Cal3} = pK_{a,mBuf} - \log\left(\frac{[mBuf_A]_{Rinse} + C2_{CO2}([CO_2]_{Cal3} - [CO_2]_{Rinse})}{[mBuf_B]_{Rinse} - C2_{CO2}([CO_2]_{Cal3} - [CO_2]_{Rinse})}\right)$$

Values for $HCO_3^-$ concentrations for Cal2 and Cal3 calibration solutions may be determined using Equation 25:

$$[HCO_3^-]_{enz,Cal2} \approx [HCO_3^-]_{Rinse} + C1_{HCO3}([HCO_3^-]_{Cal2} - [HCO_3^-]_{Rinse}) + C2_{CO2}([CO_2]_{Cal2} - [CO_2]_{Rinse})$$

$$[HCO_3^-]_{enz,Cal3} \approx [HCO_3^-]_{Rinse} + C1_{HCO3}([HCO_3^-]_{Cal3} - [HCO_3^-]_{Rinse}) + C2_{CO2}([CO_2]_{Cal3} - [CO_2]_{Rinse})$$

Values for the $Ca^{2+}$ concentration can be determined using Equation 31 for Cal2 and Cal3 calibration solutions. The $Ca^{2+}$ concentrations of previous measurements may be taken into account along with time so as to factor in the amount of enzyme modulator in the enzyme layer (331) during the measurements of the calibration solutions:

$$[Ca^{2+}]_{enz,Cal2} = [Ca^{2+}]_{Cal2} + ([Ca^{2+}]_{Rinse} + ([Ca^{2+}]_{enz,After\,last\,asp.} - [Ca^{2+}]_{Rinse})e^{-\Delta t/\tau} - [Ca^{2+}]_{Cal2})e^{-8.5/\tau} [Ca^{2+}]_{enz,Cal3} = [Ca^{2+}]_{Cal3} + ([Ca^{2+}]_{Rinse} + ([Ca^{2+}]_{enz,After\,last\,asp.} - [Ca^{2+}]_{Rinse})e^{-\Delta t/\tau} - [Ca^{2+}]_{Cal3})e^{-8.5/\tau}$$

At step 340, the sensitivity of the measuring device is calculated for each calibration solution and for the sample. This step may involve taking the measured sensitivity of a calibration solution and adjusting it by a factor, that factor being a function of modulation function and φ. φ may be given by the calibration solution sensitivities and modulation functions already calculated, and may be of the form of Equation 34:

$$\varphi_A = \frac{1}{\text{mod}_{Cal3}\left(\frac{Sens_{A,Cal2}}{Sens_{A,Cal3}} - 1\right)} + \frac{1}{\text{mod}_{Cal2}\left(\frac{Sens_{A,Cal3}}{Sens_{A,Cal2}} - 1\right)}$$

$$\varphi_B = \frac{1}{\text{mod}_{Cal3}\left(\frac{Sens_{B,Cal2}}{Sens_{B,Cal3}} - 1\right)} + \frac{1}{\text{mod}_{Cal2}\left(\frac{Sens_{B,Cal3}}{Sens_{B,Cal2}} - 1\right)}$$

Once the values for φ have been determined, and the modulation functions have been determined in steps 320 and 330, the sensitivities may be determined using Equation 33:

$$Sens_{A,sam} = Sens_{A,Cal3} \cdot \frac{1 - \frac{1}{\varphi_A \cdot \text{mod}_{sam} + 1}}{1 - \frac{1}{\varphi_A \cdot \text{mod}_{Cal3} + 1}}$$

$$Sens_{B,sam} = Sens_{B,Cal3} \cdot \frac{1 - \frac{1}{\varphi_B \cdot \text{mod}_{sam} + 1}}{1 - \frac{1}{\varphi_B \cdot \text{mod}_{Cal3} + 1}}$$

Once the sensitivities have been determined the measuring system is calibrated. From here the sensitivity for the sample may be used to determine an accurate concentration of Cr or Crn of the sample by measuring the raw output of the amperometer and dividing it by the calculated sensitivity, as expressed by Equations 1 and 2.

Figure 4:
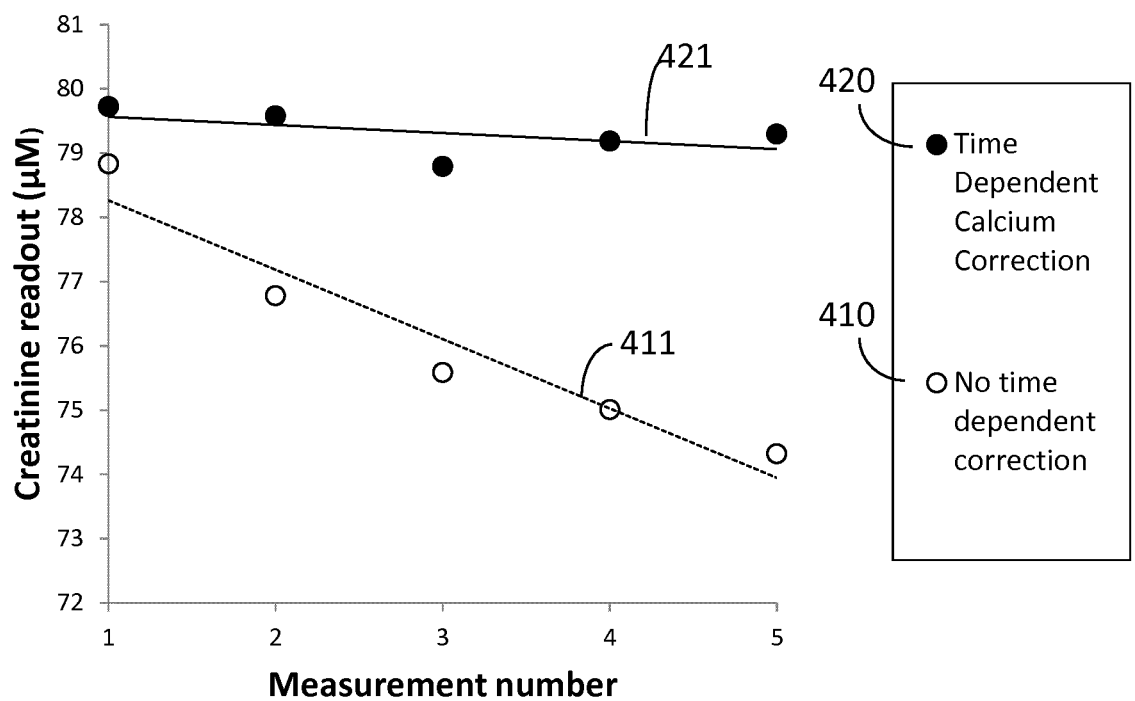
FIG. 4 is a graph illustrating the improvement in results when using the proposed method

FIG. 4 is a graph comparing the results of measuring the Crn concentrations in blood in accordance with the proposed solution, and the results without the proposed solution. A blood sample is aspirated five times with a relatively short cycle time of 2 minutes between rinsing.

The points 410 show the measurements for Crn without taking into account the amount of time-dependent enzyme modulator in the system ($Ca^{2+}$). As shown by the trend line 411, when no time dependent correction is made the measurements of Crn decrease with each subsequent measurement. This is caused by increased enzyme modulator ($Ca^{2+}$) content in the enzyme layer after each measurement where there has been insufficient rinse between measurements to clear out the $Ca^{2+}$. The data shows that the readout for Crn dropped by 5.7% (78.8 µM to 74.3 µM) over only five measurements.

The points 420 show the measurements for Crn of the same blood sample while taking into account the amount of time-dependent enzyme modulator ($Ca^{2+}$) in accordance with the proposed solution. With time-dependent corrections, the trend line 421 shows that the measurements are much more consistent across measurements, and the graph demonstrates that the proposed solution adequately accounts for the increasing levels of $Ca^{2+}$ between measurements and short rinses. The data shows that the largest variation in the Crn readings is only 1.1% (79.7 µM to 78.8 µM). This demonstrates that the proposed solutions of determining time-dependent enzyme modulation amounts can lead to more accurate and consistent results, particularly where the rinse time between measurements is short.

It is to be understood that the present disclosure includes permutations of combinations of the optional features set out in the embodiments described above. In particular, it is to be understood that the features set out in the appended dependent claims are disclosed in combination with any other relevant independent claims that may be provided, and that this disclosure is not limited to only the combination of the features of those dependent claims with the independent claim from which they originally depend.

The invention claimed is:

1. A method of calibrating a device for measuring concentration of creatine and/or creatinine in a sample including one or more enzyme modulators, the method comprising:
   providing a device for measuring concentration of creatine and/or creatinine in a sample, wherein the device comprises an enzyme layer;
   aspirating an earlier sample in the device and estimating a first concentration of an enzyme modulator remaining in the enzyme layer;
   providing one or more calibration solutions;
   determining a sensitivity of the device for each of the one or more calibration solutions;
   determining a degree of modulation for the sample to be measured;
   determining a degree of modulation for each of the one or more calibration solutions;
   wherein said determining a degree of modulation for each of the one or more calibration solutions comprises estimating a second concentration of the enzyme modulator in the enzyme layer of the device corrected by said first concentration;
   wherein the one or more enzyme modulators comprise $Ca^{2+}$, $Mg^{2+}$, and salts thereof; and
   calculating the sensitivity of the device for the sample, wherein said calculating comprises adjusting the sensitivity of the device for each of the one or more calibration solutions by a factor comprising the determined degree of modulation of the sample and the one or more calibration solutions.

2. The method of claim 1, wherein the period of time from aspirating the earlier sample to measuring the concentration of creatinine in the sample is less than two minutes.

3. The method of claim 1, wherein said estimating the second concentration of the enzyme modulator comprises determining a period of time elapsed since aspirating the earlier sample.

4. The method of claim 3, wherein the estimating the second concentration of the enzyme modulator further comprises estimating a change in the concentration of the enzyme modulator in the enzyme layer of the device during the determined period of time.

5. The method of claim 4, wherein said estimating a change in the concentration comprises evaluating an exponential decay term, wherein the time constant of the exponential decay term is related to the rate of transfer of the enzyme modulator into or out of the enzyme layer.

6. The method of claim 1, further comprising receiving a concentration of the enzyme modulator in the second sample, wherein the determination of the degree of modulation for the sample utilises the received concentration of the enzyme modulator of the sample.

7. The method of claim 1, further comprising receiving a concentration of the enzyme modulator in each of the one or more calibration solutions, wherein the determination of the degree of modulation for each of the one or more calibration solutions utilises the received concentration of the enzyme modulator of each of the one or more calibration solutions.

8. The method of claim 1, wherein prior to the determining a degree of modulation for the sample, the method further comprises performing a rinse in the device.

9. The method of claim 8, wherein said performing a rinse comprises rinsing with a rinse solution, and wherein the method further comprises receiving a concentration of the enzyme modulator of the rinse solution, wherein the determination of the degree of modulation for the sample is corrected by the concentration of the enzyme modulator of the rinse solution.

10. The method of claim 1, wherein the one or more enzyme modulators inhibit enzyme activity.

11. The method of claim 1, wherein said determining the sensitivityy of the device for each of the one or more calibration solutions comprises calculating a ratio between an output of the device and a concentration of creatinine and/or creatine in each of the one or more calibration solutions.

12. The method of claim 1, wherein said factor further comprises a ratio between two of said determined sensitivities of the one or more calibration solutions, wherein each of the one or more calibration solutions has a different amount of the enzyme modulator.

13. The method of claim 1, wherein the device comprises a creatine and/or creatinine sensor.

* * * * *

UNITED STATES PATENT AND TRADEMARK OFFICE
CERTIFICATE OF CORRECTION

PATENT NO. : 10,969,358 B2
APPLICATION NO. : 15/742121
DATED : April 6, 2021
INVENTOR(S) : Thomas Steen Hansen et al.

It is certified that error appears in the above-identified patent and that said Letters Patent is hereby corrected as shown below:

In the Claims

Claim 11, Column 22, Line 8, "sensitivityy" should read --sensitivity--.

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*